US005747328A

United States Patent [19]
Donohue et al.

[11] Patent Number: 5,747,328
[45] Date of Patent: May 5, 1998

[54] MICROBIAL SYSTEM FOR FORMALDEHYDE SENSING AND REMEDIATION

[75] Inventors: Timothy J. Donohue, Middleton; Robert D. Barber, Cross Plains; Vern Witthuhn, Madison, all of Wis.

[73] Assignee: Wisconsin Alumni Research Foundation, Madison, Wis.

[21] Appl. No.: 608,241

[22] Filed: Feb. 28, 1996

[51] Int. Cl.$^6$ .............................. C07H 21/04; C12N 1/21
[52] U.S. Cl. .................... 435/252.3; 536/23.1; 536/23.7; 536/24.1
[58] Field of Search .................... 435/6, 69.1, 252.3, 435/262.5, 320.1; 536/23.1, 23.7, 24.1

[56] References Cited

U.S. PATENT DOCUMENTS

| | | | |
|---|---|---|---|
| 4,535,061 | 8/1985 | Chakrabarty et al. | 435/252.4 |
| 4,593,003 | 6/1986 | Vandenbergh | 435/172.3 |
| 4,806,482 | 2/1989 | Horowitz | 435/262 |
| 4,833,086 | 5/1989 | Horowitz | 435/252.1 |
| 4,992,174 | 2/1991 | Caplan et al. | 210/610 |
| 5,079,166 | 1/1992 | Winter et al. | 435/262 |
| 5,196,339 | 3/1993 | Hanson et al. | 435/262 |
| 5,242,825 | 9/1993 | Mueller et al. | 435/253.3 |
| 5,283,192 | 2/1994 | Rusin | 435/252.31 |
| 5,352,608 | 10/1994 | Kaplan et al. | 435/262 |
| 5,364,787 | 11/1994 | Orser et al. | 435/252.33 |
| 5,369,029 | 11/1994 | Broker et al. | 435/262.5 |
| 5,389,525 | 2/1995 | Hollenberg et al. | 435/69.1 |
| 5,422,268 | 6/1995 | Rusin | 435/262 |
| 5,441,885 | 8/1995 | Goldberg et al. | 435/252.34 |
| 5,441,887 | 8/1995 | Hanson et al. | 435/262.5 |

OTHER PUBLICATIONS

Rott, M.A., et al. "Genetic Evidence for the Role of Isocytochrome $C_2$ in Photosynthetic Growth of *Rhodobacter sphaeroides* Spd Mutants," *J. Bateriol.* 175:358–366 (1993).

Donohue, T. Seminar given in Whitewater, Wisconsin (Dec., 1993).

Donohue, T. Seminar given in Georgia (Jan., 1994).

Donohue, T. Seminar given in Houston, Texas (Apr., 1994).

Barber, R., M. Rott, and T. Donohue. "Characterization of a Glutathione–Dependent Formaldehyde Dehydrogenase from *Rhodobacter sphaeroides*," Abstract K–66 and Poster Session presented at 94th General Meeting of American Society of Microbiology, Las Vegas, Nevada (May 23–27, 1994).

Barber, R., J. Park and T. Donohue. "Physiological role and transcriptional regulation of a glutathione–dependent formaldehyde dehydrogenase from *Rhodobacter sphaeroides*," Abstract and Poster Session presented at Cold Spring Harbor Symposium on Molecular genetics of Bacteria and Phage, Madison, Wisconsin (Aug. 2–7, 1994).

Witthuhn, V.C. and T. J. Donohue. "Identification of a two–component response regulator that controls transcription of the *adhI–cycI* operon in *Rhodobacter sphaeroides*," Abstract and Poster Session presented at Cold Spring Harbor Symposium on Molecular Genetics of Bacteria and Phage, Madison, WI (Aug. 2–7, 1994).

Barber, R., and T. Donohue. "Methanol oxydation in *Rhodobacter sphaeroides*: Role and regulation of a glutathione–dependent formaldehyde dehydrogenase," Raper Symposium, Dept. of Bacteriology, U of WI, Madison, WI (Aug., 1995).

Barber, R., M. Rott, and T. Donohue. "Characterization of a Glutathione–Dependent Formaldehyde Dehydrogenase from *Rhodobacter sphaeroides*," *J. Bacteriol.* 178 (1996).

Baumgartner, J.W., et al., "Transmembrane Signalling by a Hybrid Protein: Communication from the Domain of Chemoreceptor Trg That Recognizes Sugar–Binding Proteins to the Kinase/Phosphatase Domain of Osmosensor EnvZ," *J. Bacteriol.* 176: 1157–1163 (1994).

Chang, C., et al. "*Arabidopsis* Ethylene–Response Gene *ETR1*: Similarity of Product to Two–Component Regulators," *Science* 262: 539–544 (1993).

Harms, N., et al., "Identification of a two–component regulatory system controlling methanol dehydrogenase synthesis in *Paracoccus denitrificans*," *Mol. Microb.* 8:457–470 (1993).

Ota, I.M., and A. Varshavsky, "A Yeast Protein Similar to Bacterial Two–Component Regulators," *Science* 262: 566–569(1993).

Utsumi, R., et al., "Activation of Bacterial Porin Gene Expression by a Chimeric Signal Transducer in Response to Aspartate," *Science* 245: 1246–1249(1989).

de Vries, G.E., et al., "Physiological Regulation of *Paracoccus denitrificans* Methanol Dehydrogenase Synthesis and Activity," *J. Bacteriol.* 170: 3731–3737(1988).

Engeland, K., et al., "Mutation of Arg–115 of human class III alcohol dehydrogenase: A binding site required for formaldehyde dehydrogenase activity and fatty acid activation," *Proc. Natl. Acad. Sci. USA* 90: 2491–2494(1993).

Estonius, M., et al., "Residues Specific for Class III Alcohol Dehydrogenase Site–Directed Mutagenesis of the Human Enzyme," *Biochemistry* 33: 15080–15085(1994).

Green, D.W., et al., "Inversion of the Subtrate Specificity of Yeast Alcohol Dehydrogenase," *J. Biol. Chem.* 268: 7792–7798(1993).

Jornvall, H., et al., "Characteristics of alcohol/polyol dehydrogenases: The zinc–containing long–chain alcohol dehydrogenases," *Eur. J. Biochem.* 167: 195–201(1987).

(List continued on next page.)

*Primary Examiner*—George C. Elliott
*Assistant Examiner*—Robert Schwarteman
*Attorney, Agent, or Firm*—Quarles & Brady

[57] ABSTRACT

Environmental formaldehyde can be detected and remediated in a biological system that incorporates a bacterial cell containing suitable genetic sequences encoding a formaldehyde-inducible regulatory system. The system includes a transcriptional promoter that can be specifically induced in the presence of formaldehyde to transcribe an operably linked gene.

24 Claims, 3 Drawing Sheets

OTHER PUBLICATIONS

Koivusalo, M., and L. Uotila, "Glutathione–Dependent Formaldehyde Dehydrogenase (EC 1.2.1.1): Evidence for the Identity With Class III Alcohol Dehydrogenase," in *Enzymology and Molecular Biology of Carbonyl Metabolism 3*, ed. H. Weiner et al., Plenum Press, New York (1990).

Koivusalo, M., and L. Uotila, "Glutathione–Dependent Formaldehyde Dehydrogenase/Class III Alcohol Dehydrogenase: Further Characterization of the Rat Liver Enzyme," in *Enzymology and Molecular Biology of Carbonyl Metabolism 4*, ed. H. Weiner et al., Plenum Press, New York (1993).

Sasnauskas, K., et al., "Cloning and analysis of a *Candida maltosa* gene which confers resistance to formaldehyde in *Saccharomyces cerevisiae*," *Gene* 122:207–211 (1992).

Slooff, W., et al., "Exploratory Report Formaldehyde," National Institute of Public Health and Environmental Protection, The Netherlands (1992).

U.S. Environmental Protection Agency, "Health and Environmental Effects Profile for Formaldehyde" (1985).

Allen, L.N., and R.S. Hanson, "Construction of Broad–Host–Range Cosmid Cloning Vectors: Identification of Genes Necessary for Growth of *Methylobacterium organophilum* on Methanol," *J. Bacteriol.* 161:995–962(1985).

Dryden, S.C., and S. Kaplan, "Localization and structural analysis of the ribosomal RNA operons of *Rhodobacter sphaeroides*," *Nucleic Acids Res.* 7267–7277 (1990).

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 2408 base pairs
        ( B ) TYPE: nucleic acid
        ( C ) STRANDEDNESS: double
        ( D ) TOPOLOGY: linear -continued ( i i ) MOLECULE TYPE: DNA (genomic)

( v i ) ORIGINAL SOURCE:
    ( A ) ORGANISM: Rhodobacter sphaeroides
    ( B ) STRAIN: 2.4.1

( i x ) FEATURE:
    ( A ) NAME/KEY: -35_signal
    ( B ) LOCATION: 262..267

( i x ) FEATURE:
    ( A ) NAME/KEY: -10_signal
    ( B ) LOCATION: 285..290

( i x ) FEATURE:
    ( A ) NAME/KEY: CDS
    ( B ) LOCATION: 346..1476
    ( D ) OTHER INFORMATION: /product="AdhI Class III Alcohol Dehydrogenase Gene"

( x i ) SEQUENCE DESCRIPTION: SEQ ID NO:1:

```
GATCCGCGCG GCTGCGCGAG CTGGGGCTCG AGCCCTACGA TGCGCTCTCG CCGCCCCTGA        60

TGGATGCGAT CGCGACCCAT GTCGCGAAAC GCTCCGGCAA GCTCGCGGCC TGAGGGCTGC       120

GGCCGCTCCC TCCCGCGAGG CGGGGAGCGG CTTCTTCTGA ACGTGCCGGG CGCGGTCCGA       180

TGGCGGCAGG CCTGCCGACG CGGGACCCCC GCAGGCTTTC GCCGCAGAGG CAAGACCCGC       240

GCTCCTCATC CTTTTTTCCG AATGCCGGGC GCGGATTTTC CTCTTAAGGT CAGGCCATGA       300

CAGGCCCGAC GCCCTGCCGT CCGGTTGATT GAGAGGGAGA GTAAC ATG CGC ACC           354
                                                  Met Arg Thr
                                                    1

CGT GCC GCC GTC GCC GTC GAG GCC GGC AAG CCG CTC GAG ATC ATG GAG        402
Arg Ala Ala Val Ala Val Glu Ala Gly Lys Pro Leu Glu Ile Met Glu
      5              10                  15

GTC AAT CTC GAA GGC CCC AAG GCC GGC GAG GTC ATG GTC GAG ATC AAG        450
Val Asn Leu Glu Gly Pro Lys Ala Gly Glu Val Met Val Glu Ile Lys
 20              25                  30                  35

GCC ACC GGC ATC TGC CAC ACC GAC GAA TTC ACC CTC TCC GGC GCC GAT        498
Ala Thr Gly Ile Cys His Thr Asp Glu Phe Thr Leu Ser Gly Ala Asp
             40                  45                  50

CCC GAG GGC ATG TTC CCG GCG ATC CTC GGC CAC GAG GGC GCG GGC GTG        546
Pro Glu Gly Met Phe Pro Ala Ile Leu Gly His Glu Gly Ala Gly Val
                 55                  60                  65

GTG GTC GAG GTC GGC CCC GGC GTG ACC AGC GTG AAG CCC GGC GAT CAT        594
Val Val Glu Val Gly Pro Gly Val Thr Ser Val Lys Pro Gly Asp His
         70                  75                  80

GTG ATC CCG CTC TAC ACG CCC GAG TGC CGG CAG TGC CCC TCC TGC CTC        642
Val Ile Pro Leu Tyr Thr Pro Glu Cys Arg Gln Cys Pro Ser Cys Leu
     85                  90                  95

AGC CAG AAG ACG AAC CTC TGC ACC GCG ATC CGC GGC ACG CAG GGG CAG        690
Ser Gln Lys Thr Asn Leu Cys Thr Ala Ile Arg Gly Thr Gln Gly Gln
100                 105                 110                 115

GGG CTG ATG CCC GAC GGC ACC AGC CGC TTC TCG ATG CTC GAT GGC ACG        738
Gly Leu Met Pro Asp Gly Thr Ser Arg Phe Ser Met Leu Asp Gly Thr
                120                 125                 130

CCG ATC CTG CAT TAC ATG GGC TGC TCG ACC TTC TCG AAC TAC ACG GTC        786
Pro Ile Leu His Tyr Met Gly Cys Ser Thr Phe Ser Asn Tyr Thr Val
            135                 140                 145

CTG CCC GAG ATC GCG GTG GCG AAG GTG CGC CCG GAT GCG CCC TTC GAC        834
Leu Pro Glu Ile Ala Val Ala Lys Val Arg Pro Asp Ala Pro Phe Asp
        150                 155                 160

AAG ATC TGC TAC ATC GGC TGC GGC GTC ACC ACC GGC ATC GGC GCG GTC        882
Lys Ile Cys Tyr Ile Gly Cys Gly Val Thr Thr Gly Ile Gly Ala Val
    165                 170                 175
```

```
ATC AAC ACG GCC AAG GTC GAG ATC GGC GCC AAG GCC GTG GTG TTC GGG      930
Ile Asn Thr Ala Lys Val Glu Ile Gly Ala Lys Ala Val Val Phe Gly
180             185             190             195

CTG GGC GGC ATC GGT CTC AAC GTG ATC CAG GGC CTG AAG CTC GCG GGC      978
Leu Gly Gly Ile Gly Leu Asn Val Ile Gln Gly Leu Lys Leu Ala Gly
                200             205             210

GCC GAC ATG ATC ATC GGC GTG GAT CTG AAC AAC GCC AAG AAG GAA TGG     1026
Ala Asp Met Ile Ile Gly Val Asp Leu Asn Asn Ala Lys Lys Glu Trp
            215             220             225

GGC GAG CGC TTC GGC ATG ACC CAT TTC GTG AAT CCG TCC GAG ATC GAC     1074
Gly Glu Arg Phe Gly Met Thr His Phe Val Asn Pro Ser Glu Ile Asp
        230             235             240

GGC GAT GTG GTG GCG CAT CTG GTC AAT ATG ACC AAG ACG CCC TTC GAC     1122
Gly Asp Val Val Ala His Leu Val Asn Met Thr Lys Thr Pro Phe Asp
245             250             255

CAG ATC GGC GGG GCG GAC TAC ACC TTC GAC TGC ACC GGC AAC GTG AAG     1170
Gln Ile Gly Gly Ala Asp Tyr Thr Phe Asp Cys Thr Gly Asn Val Lys
260             265             270             275

GTG ATG CGT CAG GCG CTG GAG GCG TGC CAT CGT GGC TGG GGC CAG TCG     1218
Val Met Arg Gln Ala Leu Glu Ala Cys His Arg Gly Trp Gly Gln Ser
            280             285             290

ATC GTG ATC GGT GTG GCG CCG GCG GGG GCC GAG ATC CAG ACG CGG CCG     1266
Ile Val Ile Gly Val Ala Pro Ala Gly Ala Glu Ile Gln Thr Arg Pro
        295             300             305

TTC CAG CTG GTG ACG GGG CGG GTC TGG AAG GGC TCG GCC TTC GGC GGC     1314
Phe Gln Leu Val Thr Gly Arg Val Trp Lys Gly Ser Ala Phe Gly Gly
    310             315             320

GCG CGC GGC CGG ACC GAC GTG CCG AAG ATC GTC GAC TGG TAC ATG GAG     1362
Ala Arg Gly Arg Thr Asp Val Pro Lys Ile Val Asp Trp Tyr Met Glu
325             330             335

GGC AAG ATC CAG ATC GAC CCG ATG ATC ACC CAC ATC CTG AGC CTC GAA     1410
Gly Lys Ile Gln Ile Asp Pro Met Ile Thr His Ile Leu Ser Leu Glu
340             345             350             355

GAG ATC AAC AAG GGC TTC GAC CTC ATG CAC GCG GGC GAG TCC ATC CGC     1458
Glu Ile Asn Lys Gly Phe Asp Leu Met His Ala Gly Glu Ser Ile Arg
            360             365             370

TCG GTC GTG GTG TTC TGA TCGGCCACCC CTCCAAGACG GTGACGATTT            1506
Ser Val Val Val Phe  *
            375

CCCGAGTAAC GGTGCCAGCG ACCCGGCCGG TCCCTTGACC GGCCGCGGGC GGCCTGCCGC   1566

GCAGGACGCC CCCGAGCCAT CCGCAAAGGG AGAAGACCAT GAGATTGACC ACCATCCTCG   1626

CCGGGGCGCT CGCTCTCGGT GCCGCGCAGG CCGCCTTCGC CGAAGGCGAC CCGGCGGCCG   1686

GCGAGAAGGC CTTCCGGAAA TGTCAGGCCT GCCACCAGAT CGGCGCCGAG CGCAGAACA    1746

AGACCGGGCC CGTCCTGACC GGCGTCATCG GTCGCCCGGC GGCCTCGATC GAGGGCTTCA   1806

GCTATTCCAA GACCCTGACC GAGGCCGCGG CCGATGGCCT CGTCTGGGAT CATGCTGCGC   1866

TCGAGACCTT CCTGGCCAAT CCGCGCAAGG CGATGCCGGG CACCAAGATG GCCTTCCCCG   1926

GCATCAAGAA ACCGCAGGAG CTGGCCGACA TCCTGGCCTA TCTCGACACC TTCTCGGACG   1986

GGGAAACGCG GGAGGCCGAA GAGACCCCCG CGGCGGCGCC GGCGGAGGGC TGAAATGCCT   2046

GTCTGCCAAG GCTTTCGCCC TCGTCATGGC GCCACCGGCG ATCGTCATAC TTTGGGCTTA   2106

AAGCGGGACC GCAGCGTTAA CGCTTCAAAT CGGCGCGCCG TAGCATGAGG TTCGGTGACA   2166

GGTCGGCAGC TCCGGGGAGG GAGCCGCGAC CGGTGAAGAT CACGAGCCAA TTTCAAGAAA   2226

TCAACATCGG GAGGAGCCAA TGAAGATGCT GAAGACGGGT CTCGTAGCGA CCCTATTGCT   2286

CTCGTCTCGC GGCCAGAACG GTTGCTGAGC CAGGAGTTCC GCTGGCTGCT AGGCTTCGTC   2346
```

ACCCGCTAGG TCTGGCCGCT TGATACGGTT GTGGGCGATA AGGCTCGACT TGGTCTAGTG    2406

GG    2408

( 2 ) INFORMATION FOR SEQ ID NO:2:

( i ) SEQUENCE CHARACTERISTICS:
    ( A ) LENGTH: 376 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Met Arg Thr Arg Ala Ala Val Ala Val Glu Ala Gly Lys Pro Leu Glu
 1               5                  10                  15

Ile Met Glu Val Asn Leu Glu Gly Pro Lys Ala Gly Glu Val Met Val
            20                  25                  30

Glu Ile Lys Ala Thr Gly Ile Cys His Thr Asp Glu Phe Thr Leu Ser
        35                  40                  45

Gly Ala Asp Pro Glu Gly Met Phe Pro Ala Ile Leu Gly His Glu Gly
    50                  55                  60

Ala Gly Val Val Val Glu Val Gly Pro Gly Val Thr Ser Val Lys Pro
65                  70                  75                  80

Gly Asp His Val Ile Pro Leu Tyr Thr Pro Glu Cys Arg Gln Cys Pro
                85                  90                  95

Ser Cys Leu Ser Gln Lys Thr Asn Leu Cys Thr Ala Ile Arg Gly Thr
            100                 105                 110

Gln Gly Gln Gly Leu Met Pro Asp Gly Thr Ser Arg Phe Ser Met Leu
        115                 120                 125

Asp Gly Thr Pro Ile Leu His Tyr Met Gly Cys Ser Thr Phe Ser Asn
    130                 135                 140

Tyr Thr Val Leu Pro Glu Ile Ala Val Ala Lys Val Arg Pro Asp Ala
145                 150                 155                 160

Pro Phe Asp Lys Ile Cys Tyr Ile Gly Cys Gly Val Thr Thr Gly Ile
                165                 170                 175

Gly Ala Val Ile Asn Thr Ala Lys Val Glu Ile Gly Ala Lys Ala Val
            180                 185                 190

Val Phe Gly Leu Gly Gly Ile Gly Leu Asn Val Ile Gln Gly Leu Lys
        195                 200                 205

Leu Ala Gly Ala Asp Met Ile Ile Gly Val Asp Leu Asn Asn Ala Lys
    210                 215                 220

Lys Glu Trp Gly Glu Arg Phe Gly Met Thr His Phe Val Asn Pro Ser
225                 230                 235                 240

Glu Ile Asp Gly Asp Val Val Ala His Leu Val Asn Met Thr Lys Thr
                245                 250                 255

Pro Phe Asp Gln Ile Gly Gly Ala Asp Tyr Thr Phe Asp Cys Thr Gly
            260                 265                 270

Asn Val Lys Val Met Arg Gln Ala Leu Glu Ala Cys His Arg Gly Trp
        275                 280                 285

Gly Gln Ser Ile Val Ile Gly Val Ala Pro Ala Gly Ala Glu Ile Gln
    290                 295                 300

Thr Arg Pro Phe Gln Leu Val Thr Gly Arg Val Trp Lys Gly Ser Ala
305                 310                 315                 320

Phe Gly Gly Ala Arg Gly Arg Thr Asp Val Pro Lys Ile Val Asp Trp
                325                 330                 335

Tyr Met Glu Gly Lys Ile Gln Ile Asp Pro Met Ile Thr His Ile Leu
```

```
                      340                        345                         350
Ser  Leu  Glu  Glu  Ile  Asn  Lys  Gly  Phe  Asp  Leu  Met  His  Ala  Gly  Glu
               355                      360                      365

Ser  Ile  Arg  Ser  Val  Val  Val  Phe
          370                     375
```

( 2 ) INFORMATION FOR SEQ ID NO:3:

( i ) SEQUENCE CHARACTERISTICS:
        ( A ) LENGTH: 1058 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Rhodobacter sphaeroides
        ( B ) STRAIN: 2.4.1

( v i i ) IMMEDIATE SOURCE:
        ( B ) CLONE: pUI8017

( i x ) FEATURE:
        ( A ) NAME/KEY: CDS
        ( B ) LOCATION: 221..895

( x i ) SEQUENCE DESCRIPTION: SEQ ID NO:3:

```
GGATCCGGGC  ATGCCTGCGG  CCGAAGGATG  CGGGAACCGT  CCGCACCGAC  AGATGCGCGA          60

ACCGTATGGC  CGGCCGGGAA  GTGGGGGGCT  CCGCTCTCTC  GGTAAGAACA  GGTCGGTCGC         120

GCCGTAGCGG  CAAGGGCGCC  GGTGCTCCGA  CCTTTGGCCG  GGTTATCGCG  TCAGGCGGAT         180

GTGCTAGCCT  CGTGAAAAGA  CGTATGGGAC  CGCC ATG ATG CAA CCT TCC CGC               232
                                        Gln Pro Ser Arg
                                         1

CCG CTC CAG TCC GCG CTG ATC GTC GAC GAT CAT CCG CTC TTC TGC GAT               280
Pro Leu Gln Ser Ala Leu Ile Val Asp Asp His Pro Leu Phe Cys Asp
  5              10                  15                  20

GCG CTG TCG ATG ACG CTC AAG GCG GTG GCG GGA CTG ACC CAC ATC GAA               328
Ala Leu Ser Met Thr Leu Lys Ala Val Ala Gly Leu Thr His Ile Glu
             25                  30                  35

TCC GCC GAC CGG CTC GAG ACC GCT CTG GCC CGG CTC GAC CTG CAG CCG               376
Ser Ala Asp Arg Leu Glu Thr Ala Leu Ala Arg Leu Asp Leu Gln Pro
         40                  45                  50

GCG TTC GAT GTG GTG GTG CTG GAT CTG AAC CTG CCG GAC GTG AAC GGC               424
Ala Phe Asp Val Val Val Leu Asp Leu Asn Leu Pro Asp Val Asn Gly
     55                  60                  65

CTC GAC GGC CTC ATC CGT CTG AAG GCG AGC CCC GGG GCG GTG CCG GTG               472
Leu Asp Gly Leu Ile Arg Leu Lys Ala Ser Pro Gly Ala Val Pro Val
 70                  75                  80

GTG GTG GTC TCT TCC CTC GCC GAC AAC CGG GTG ATC GGG GCG GCG CTG               520
Val Val Val Ser Ser Leu Ala Asp Asn Arg Val Ile Gly Ala Ala Leu
 85                  90                  95                 100

AAG GCG GGT GCG GCG GGC TTC GTG CCC AAG CAC TCC CGC CGC GAG GTG               568
Lys Ala Gly Ala Ala Gly Phe Val Pro Lys His Ser Arg Arg Glu Val
                    105                 110                 115

TTC CGC GCG GCC TTC GAT GCG ATC CGC GAA GGG CGC AGC TAC CTG CCC               616
Phe Arg Ala Ala Phe Asp Ala Ile Arg Glu Gly Arg Ser Tyr Leu Pro
                120                 125                 130

GAA GAT TCA CGC CTC ATT CCC CCG GGC GCG CCC GCC AGC CAG CGC GAG               664
Glu Asp Ser Arg Leu Ile Pro Pro Gly Ala Pro Ala Ser Gln Arg Glu
            135                 140                 145

GAA GCC ATC GCA CGG CTT GCG CTC GTC ACG CGG CAG CAG GCG AAG ATC               712
Glu Ala Ile Ala Arg Leu Ala Leu Val Thr Arg Gln Gln Ala Lys Ile
```

```
          150                         155                         160
CTC  CAG  CTC  ATC  TGC  GAG  GGG  CGG  CTG  AAC  AAG  CAG  ATC  GCC  TAT  GAC      760
Leu  Gln  Leu  Ile  Cys  Glu  Gly  Arg  Leu  Asn  Lys  Gln  Ile  Ala  Tyr  Asp
165                      170                      175                      180

CTG  ACC  ATC  GCC  GAG  ACG  ACC  GTG  AAG  GCC  CAT  GTC  ACG  GCC  ATT  ATG      808
Leu  Thr  Ile  Ala  Glu  Thr  Thr  Val  Lys  Ala  His  Val  Thr  Ala  Ile  Met
                         185                      190                      195

CGC  AAG  CTC  GGC  GTC  CAG  AGC  CGG  ACC  CAG  GCG  GTG  CTC  ATG  GTG  CAG      856
Arg  Lys  Leu  Gly  Val  Gln  Ser  Arg  Thr  Gln  Ala  Val  Leu  Met  Val  Gln
               200                      205                      210

GAG  GCG  AGC  TTC  GCG  AGC  CTG  ATG  CCG  GAA  AAT  TCC  TGA  CAGCCGGTTG          905
Glu  Ala  Ser  Phe  Ala  Ser  Leu  Met  Pro  Glu  Asn  Ser   *
          215                      220

GGCAGCGGCT  GCGCGCTTCG  GGGGCCTGTC  GAACGGCTTG  TCAGCCGTTG  CGGGCAGCAG              965

ATTAGGTTTG  CTGGCTGGGA  GGACGGCGAT  GGAAGGAACT  TCGCGAGCGG  CGCCGGTCGC             1025

GGCGGAGGCG  AACGGCGCCC  CGCTGGTGCG  GAG                                            1058
```

( 2 ) INFORMATION FOR SEQ ID NO:4:

( i ) SEQUENCE CHARACTERISTICS:
        ( A ) LENGTH: 224 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
          Gln  Pro  Ser  Arg  Pro  Leu  Gln  Ser  Ala  Leu  Ile  Val  Asp  Asp
           1                   5                        10

His  Pro  Leu  Phe  Cys  Asp  Ala  Leu  Ser  Met  Thr  Leu  Lys  Ala  Val  Ala
 15                      20                        25                        30

Gly  Leu  Thr  His  Ile  Glu  Ser  Ala  Asp  Arg  Leu  Glu  Thr  Ala  Leu  Ala
                     35                        40                        45

Arg  Leu  Asp  Leu  Gln  Pro  Ala  Phe  Asp  Val  Val  Leu  Asp  Leu  Asn
                50                        55                        60

Leu  Pro  Asp  Val  Asn  Gly  Leu  Asp  Gly  Leu  Ile  Arg  Leu  Lys  Ala  Ser
           65                        70                        75

Pro  Gly  Ala  Val  Pro  Val  Val  Val  Ser  Ser  Leu  Ala  Asp  Asn  Arg
      80                        85                        90

Val  Ile  Gly  Ala  Ala  Leu  Lys  Ala  Gly  Ala  Ala  Gly  Phe  Val  Pro  Lys
 95                       100                      105                      110

His  Ser  Arg  Arg  Glu  Val  Phe  Arg  Ala  Ala  Phe  Asp  Ala  Ile  Arg  Glu
                    115                      120                      125

Gly  Arg  Ser  Tyr  Leu  Pro  Glu  Asp  Ser  Arg  Leu  Ile  Pro  Pro  Gly  Ala
               130                      135                      140

Pro  Ala  Ser  Gln  Arg  Glu  Glu  Ala  Ile  Ala  Arg  Leu  Ala  Leu  Val  Thr
          145                      150                      155

Arg  Gln  Gln  Ala  Lys  Ile  Leu  Gln  Leu  Ile  Cys  Glu  Gly  Arg  Leu  Asn
     160                      165                      170

Lys  Gln  Ile  Ala  Tyr  Asp  Leu  Thr  Ile  Ala  Glu  Thr  Thr  Val  Lys  Ala
175                      180                      185                      190

His  Val  Thr  Ala  Ile  Met  Arg  Lys  Leu  Gly  Val  Gln  Ser  Arg  Thr  Gln
                    195                      200                      205

Ala  Val  Leu  Met  Val  Gln  Glu  Ala  Ser  Phe  Ala  Ser  Leu  Met  Pro  Glu
               210                      215                      220

Asn  Ser
```

( 2 ) INFORMATION FOR SEQ ID NO:5:

( i ) SEQUENCE CHARACTERISTICS:
  ( A ) LENGTH: 2563 base pairs
  ( B ) TYPE: nucleic acid
  ( C ) STRANDEDNESS: double
  ( D ) TOPOLOGY: linear ( i i ) MOLECULE TYPE: DNA (genomic)

( v i ) ORIGINAL SOURCE:
  ( A ) ORGANISM: Rhodobacter sphaeroides
  ( B ) STRAIN: 2.4.1

( v i i ) IMMEDIATE SOURCE:
  ( B ) CLONE: pUI8017

( i x ) FEATURE:
  ( A ) NAME/KEY: CDS
  ( B ) LOCATION: 2113..2400
  ( D ) OTHER INFORMATION: /product="Partial Sensor Coding Sequence"

( x i ) SEQUENCE DESCRIPTION: SEQ ID NO:5:

| | | | | | | |
|---|---|---|---|---|---|---|
| GGCGACTATC | AGCGCCGAGG | GCTATACCGA | AGGCAGGTGG | TGGCGGTGGC | GCTTCCCGCC | 60 |
| GCCCATTTCC | ACGTCCGGCC | CATCCTGATC | GGGGCTTTGG | CCGATCTCGA | CCGCGAGGAA | 120 |
| CTGATCGGCC | GCCTCATCCG | CGAGCGGGAT | CTGGCGCGCG | AGCGGCCCGA | CTGGGCCGCG | 180 |
| AATTCCGCCT | TCCTCATGGT | GGACGGGCTG | TCGACGCGCG | AGGACGAACT | GGCCTCGACG | 240 |
| CTCGCCGCGG | GGCTGGGGCC | GGTGCCGCTC | TTCGGCGGCT | CGGCCGCGAA | CGGGTGCGCT | 300 |
| GGCGCGAGAC | CTTCGTGATC | CATGGCGCCG | ATGTCCTGAG | GGACGCGGCG | GTGCTGGCGC | 360 |
| TGGTGCGGAG | ACTGCCGGGT | GCGGGTGTTC | AACCTCGACC | ATTTCCGCCC | CACCGATCAG | 420 |
| CGCATGGTCG | TCACCGAGGC | CGATCCCGCG | CGCCGCATCG | TGCGCCGGAT | CAATGCGCGG | 480 |
| CGCAGGAATA | TCGCCCGGCT | GCTCGGCAAG | GATCCGGGGC | AGCTCGACAG | CTTCACCTTC | 540 |
| GCGGCCCATC | CGGTGGTGGT | GCGGATCGGC | GGCAAGCATC | ACGTCCGCGC | CATCCGCGAG | 600 |
| GTCGCGCCGA | ACGCGATCTC | GTCGGCTTTC | CGCATCGACG | AGGGGCTGGT | GCTTGCCCTG | 660 |
| GCCGAACCGC | AGGATCTCGT | CGGGCATCTG | ACGGACGAGC | TGGCGGGGCT | GGGCGCGCGA | 720 |
| GGCGAGCCCT | CGGCCATTGT | CGCGTGCGAT | TGCGTGCTGC | GCCGGATGGA | GGCGCTCGAC | 780 |
| AGCCAGTCCA | TCGGGCGGT | CTCGGCCCTT | CTGCGGCGGC | ATCGCGTGGT | GGGCTTCTCG | 840 |
| ACCTACGGCG | AGCAGCTGAA | CGGGAATGCA | TGTATGCATG | TGAACCAGAC | CATGACCGGG | 900 |
| GTCGCGATCT | ACCCGCCGGG | AGGAGCGATG | AGGGCGGGCC | GGGGCGGTGA | CCTGCGTCCC | 960 |
| AGTGGGGGAA | GGACCATGCG | CCACGCGGAG | CGGAGCGACA | TGAGCCTTCC | TCTGATCGAT | 1020 |
| CCCAGCGATC | CGCCCGAGCG | ACAGGCGACA | AGCTTCTCGA | GATCGTGCGC | GCGCTGATGG | 1080 |
| CGCGGGTGGA | GCGCTCGACC | GACGACGCGT | GCCAGGCTAT | GCGCAGTCCA | GCGCGCCGCC | 1140 |
| ATGCTCGAGG | ATCAGGTGCG | CGAGGCACAG | CGGATCTGCC | AGCGCACGCT | GGAACTGCTG | 1200 |
| AACCTCTCGA | ACGAGCGGCT | GGCGGAAGCC | ACGCGCGCGG | CCGACCAGGT | GCGCCAGAAC | 1260 |
| CTCGCCAATG | CCATCGAGAC | GGTGCAGGAG | GGCTTCGCGC | TCTTGGATGC | CGACGATGTG | 1320 |
| CTCGTGCTGT | GCAATTTTCC | GCGCTTCGGG | ATGCACATGC | TCGACATTCA | GGAGCATCTG | 1380 |
| AGGCCCGGCC | TCTCGCTTCG | GCGGCTATAT | CGACCGCTTG | AGCGTTCGCG | GTATCTGGCG | 1440 |
| CTGCCCGAGG | CGGAGACACC | CGAGGATTTG | GGCGGTCCGG | CGCAAGCGCG | GCACTACGAC | 1500 |
| CCCCATTCGA | TCTTCAACGT | GCGGCTGATC | TGGGACCGCT | GGCTGCAGGT | CTCCGAGCAT | 1560 |
| CGGACGGCCG | ATGGCGGCAC | GGTGATCCTG | CAGACCGACG | TGACCGACCT | GATCCGCATC | 1620 |

| GAGCGGCTCG | AGCGCGGCAA | GATGCTCGAC | GATCAGGCCC | GCCGTTATCC | GCGCGTACGC | 1680 |
| AGCTCGCATC | ACATCAATCA | GGGGGTCTGC | ATCTTCGATG | CCGAGGGGCG | GCTCGTCGGC | 1740 |
| TGGAACCAGC | GCCTCGGCTC | GCTGCTCGCG | ATCCCGATGA | ACCGCTTCCG | GCTGGGGGTG | 1800 |
| AGCTTCGGCT | ACCTGCTCGA | ACGGTTCGCG | CACGAGATCA | GCTTCGGCGA | GGGCATGGAT | 1860 |
| GCGGCCCATC | TCGAGGCCTG | GGTCCAGGCC | GCGCCACGAA | CGCGCGCGCG | CTCTCTTTCG | 1920 |
| AGCCTCCGCC | GCCACGACGA | GCTGATCCTC | GATGTCTTCG | CCGCAGGAAG | ATGCCCCACC | 1980 |
| GCGGCTTCGT | GATGAGTTTC | ACCGACGTCA | CGCCGAGCGG | GCCCCGCCA  | TCGATGCGCT | 2040 |
| GAGCCGTGCG | AACGAAAACG | TTCGAGGCGC | GGGTGATGGA | GCGGACGCTG | GAGCTCGAGG | 2100 |

```
ATGCGCTCCC TT GGG TCA TGC CGA CGG GCC AAT GGG TCG CGC TCG CGC      2148
              Gly Ser Cys Arg Arg Ala Asn Gly Ser Arg Ser Arg
              1               5                   10

TTC GTG GCG GCG GCG AGC CAC GAT CTG TTG CAG CCG CTG TCG GCG GCC    2196
Phe Val Ala Ala Ala Ser His Asp Leu Leu Gln Pro Leu Ser Ala Ala
        15              20                  25

AAG CTC TTC ATC GCC ACC ATC GGC GAC GAG GCG GTG GCG CCC GAA AGC    2244
Lys Leu Phe Ile Ala Thr Ile Gly Asp Glu Ala Val Ala Pro Glu Ser
    30              35                  40

CGC GAG GCG CTG ACC AAG GCG CAG AAG GCG CTC GAC TCG GTG GAG GGG    2292
Arg Glu Ala Leu Thr Lys Ala Gln Lys Ala Leu Asp Ser Val Glu Gly
45              50                  55                  60

ATC CTC GGC GCG CTT CTC GAC ATC TCG AAA CTC GAG TCG GGC CGG GCG    2340
Ile Leu Gly Ala Leu Leu Asp Ile Ser Lys Leu Glu Ser Gly Arg Ala
            65                  70                  75

GCG GTC TCG ATC CAG CCG GTG CGC CTC GAC CGG CTG ATG GCG GAG CTC    2388
Ala Val Ser Ile Gln Pro Val Arg Leu Asp Arg Leu Met Ala Glu Leu
                80                  85                  90

TCC GAC GAA TTC GCGCCCATCG CCGCGGCGGC GCGCGGCCTC CGGCTCACGG        2440
Ser Asp Glu Phe
            95
```

| TGCAGCCCTC | GAGCGCGGTG | GTGGCCTCCG | ACCCGACCTA | TCTCCGGCGG | ATCCTCCAGA | 2500 |
| ACCTGATCGG | CAATGCGATC | CGCTACACCG | CGAAGGCAGG | TGCTTCTCGC | GCGCGGATGA | 2560 |
| ACC | | | | | | 2563 |

( 2 ) INFORMATION FOR SEQ ID NO:6:

( i ) SEQUENCE CHARACTERISTICS:
        ( A ) LENGTH: 96 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Gly Ser Cys Arg Arg Ala Asn Gly Ser Arg Ser Arg Phe Val Ala Ala
1               5                   10                  15

Ala Ser His Asp Leu Leu Gln Pro Leu Ser Ala Ala Lys Leu Phe Ile
            20                  25                  30

Ala Thr Ile Gly Asp Glu Ala Val Ala Pro Glu Ser Arg Glu Ala Leu
        35                  40                  45

Thr Lys Ala Gln Lys Ala Leu Asp Ser Val Glu Gly Ile Leu Gly Ala
    50                  55                  60

Leu Leu Asp Ile Ser Lys Leu Glu Ser Gly Arg Ala Ala Val Ser Ile
65                  70                  75                  80

Gln Pro Val Arg Leu Asp Arg Leu Met Ala Glu Leu Ser Asp Glu Phe
                85                  90                  95
```

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide
            complementary to region downstream of adhI translation
            start codon"

(xi) SEQUENCE DESCRIPTION: SEQ ID NO:7:

ATTGACCTCC ATGATCTCGA                                           20

MICROBIAL SYSTEM FOR FORMALDEHYDE SENSING AND REMEDIATION

STATEMENT REGARDING FEDERALLY SPONSORED RESEARCH

This invention was made with United States Government support awarded by USDA, USDA Project Numbers 37262-5588 and 37306-0336; Hatch Project Number 3766. The United States Government has certain rights in this invention.

FIELD OF THE INVENTION

The present invention relates to the fields of biosensing and bioremediation and more particularly to the field of sensing and remediating formaldehyde.

BACKGROUND OF THE INVENTION

Increasing concern over environmental contaminants has made desirable systems for detecting and remediating such contaminants. Among the more important contaminants of industrial societies is formaldehyde. The health and environmental effects of formaldehyde have been well characterized, as has their distribution in soil and water. See, e.g. "Health and Environmental Effects Profile for Formaldehyde," Report No. EPA/600/X-85/362, Environmental Criteria and Assessment Office, Office of Health and Environmental Assessment, Office of Research and Development, US Environmental Protection Agency, Cincinnati, Ohio 45268 (NTIS document number PB88-174958) (October 1985) and "Exploratory Report Formaldehyde," Report No. 710401018, National Institute of Public Health and Environmental Protection, Bilthoven, The Netherlands (NTIS Report No. PB93-224483) (October 1992).

Evidence of formaldehyde carcinogenicity in rats and other epidemiological evidence have led to the classification of this compound as a probable human carcinogen. Formaldehyde is a common product of several industries (wood processing, paper production) that feed run-offs into aquatic ecosystems. Formaldehyde, which is present in approximately 2,000 entries of the Product Register Data Base, is also released from common cleaning agents, soaps, shampoos, paints, and lacquers. Little is known about how cells sense this toxin, metabolize it, or control the genes that are required for formaldehyde oxidation.

Existing chemical monitors for formaldehyde are time-consuming, exhibit variable sensitivity, and are prone to cross-reactivity with other aldehydes. It would be useful to utilize a biological system capable of specific response to, and detection of, formaldehyde. Moreover, a system capable of responding in the presence of formaldehyde could be useful as a bioremediation tool to reduce or eliminate formaldehyde as an environmental contaminant. However, to date, no biological formaldehyde-inducible detection or remediation system has been constructed.

Most organisms have the ability, using various metabolic pathways, to generate both energy and carbon skeletons by oxidizing a wide spectrum of substrates, including substrates that are themselves environmental toxins. Formaldehyde oxidation can be mediated by Class III alcohol dehydrogenase enzymes, also called glutathione-dependent formaldehyde-dehydrogenases or GSH-FDH, which are a well studied class of the zinc-dependent alcohol dehydrogenase protein family that is known in both prokaryotes and eukaryotes.

GSH-FDH enzymes are believed to perform different functions depending upon the cell type. In some organisms, GSH-FDH serves a role in the catabolism of methylated compounds. For example, some methylotrophic microbes use GSH-FDH to generate carbon skeletons and NADH from the formaldehyde that is produced from methanol oxidation. In non-methylotrophic organisms, GSH-FDH rids the cells of toxic formaldehyde produced from the oxidation of methylated substrates such as choline, sarcosine, methionine, O-methylated amino acids, methanol, methyl halides, or several N-, O-, or S-methylated xenobiotics. In both roles, GSH-FDH enzymes generate reducing power, NADH, and a product, S-formylglutathione, that can be subsequently oxidized to generate one-carbon compounds such as formate or carbon dioxide.

In particular, S-hydroxy methyl glutathione (HMGSH), an adduct formed spontaneously by glutathione (GSH) and formaldehyde (HCHO) (reaction 1), is both the preferred in vitro substrate and the presumed physiologically relevant substrate in vivo for GSH-FDH enzymes (reaction 2).

(1) HCHO+GSH→HMGSH (spontaneous) 

(2) HMGSH+NAD$^+$→S-formylglutathione+NADH+H$^+$ 

Unlike other classes of alcohol dehydrogenase enzymes, members of the GSH-FDH family do not exhibit appreciable activity with short aliphatic alcohol substrates such as ethanol. Instead, GSH-FDH enzymes catalyze the NAD-dependent oxidation of long chain hydroxylated fatty acids (i.e., 12-hydroxydodecanoic acid) or long chain alcohols.

In the photosynthetic purple bacterium *Rhodobacter sphaeroides*, a glutathione-dependent formaldehyde dehydrogenase protein (AdhI) is encoded by adhI in an operon that also includes cycI which encodes an isoform of the cytochrome $c_2$ family of electron transport proteins. The AdhI protein encoded by adhI has the characteristic substrate preference of a glutathione-dependent formaldehyde dehydrogenase. Ferguson plot analysis, using zymograms, suggests that the functional form of AdhI is a homodimer of approximately 40 kDa subunits, analogous to other such enzymes. The complete nucleotide sequence of *R. sphaeroides* adhI has not heretofore been disclosed.

Expression of the adhI-cycI operon is thought to be regulated since the abundance of isocytochrome $c_2$ was increased by a trans-acting regulatory mutation. Rott, et al., "Genetic Evidence for the Role of Isocytochrome $c_2$ in Photosynthetic Growth of *Rhodobacter sphaeroides* Spd Mutants," *J. Bacteriol.* 175:358–66 (1993).

SUMMARY OF THE INVENTION

The present invention is summarized in that a protein-encoding genetic sequence that is operably linked to a formaldehyde-inducible transcriptional promoter sequence and a cis-acting operator in a genetic construct can be specifically transcribed in a bacterial host cell that contains a formaldehyde-specific regulatory system disclosed herein, when the cell is exposed to formaldehyde. The genetic construct is useful in an assay for detecting formaldehyde.

The invention is further summarized in that a formaldehyde dehydrogenase gene that is operably linked to the formaldehyde-inducible transcriptional promoter/operator sequence in a genetic construct can be specifically transcribed in a bacterial host cell that contains the formaldehyde-specific regulatory system when the cell is exposed to formaldehyde, thereby producing a formaldehyde dehydrogenase enzyme. The construct is useful in a bioremediation assay capable of metabolizing formaldehyde into single-carbon skeletons.

The invention is further summarized in that a bacterial cell can respond in a biosensing assay or bioremediation assay if it contains a genetic construct that includes a protein-encoding genetic sequence operably linked to the formaldehyde-inducible transcriptional promoter sequence linked to a cis-acting operator, a trans-acting regulator of the transcriptional promoter and a formaldehyde-specific sensor molecule.

When linked to the cis-acting operator sequence described herein, the transcriptional promoter can be induced in the presence of formaldehyde to transcribe the operably linked protein-encoding sequence in the presence of a two-component regulatory system wherein a first component senses the presence of formaldehyde and a second component regulates transcription of the protein-encoding sequence. The sensor molecule and the regulator molecule can be provided as proteins or can be encoded on a genetic construct when placed under the control of a suitable promoter. The gene or genes encoding the sensor and/or regulator can be provided on the same construct as the formaldehyde-inducible promoter operably linked to the coding sequence, or can be provided on separate constructs. If provided on the same construct, the gene or genes should be under the transcriptional control of an unregulated or constitutive promoter.

The present invention is also summarized in that a method for detecting the presence of formaldehyde includes the steps of (1) adding to a sample to be tested a bacterial cell that contains (a) a genetic construct that includes a genetic sequence encoding a detectable protein operably linked to the disclosed promoter/operator sequence, and further contains (b) a trans-acting regulator of the formaldehyde-specific transcriptional promoter as well as (c) a formaldehyde-specific sensor molecule, and then (2) monitoring for the presence of the detectable protein.

The present invention is also summarized in that a method for remediating formaldehyde from an environment includes the steps of (1) adding to a formaldehyde-containing sample a bacterial cell that contains (a) a genetic construct that includes a formaldehyde dehydrogenase gene operably linked to the promoter/operator sequence disclosed herein, and further contains (b) a trans-acting regulator of the transcriptional promoter and (c) a formaldehyde-specific sensor molecule, and then (2) monitoring a decrease in formaldehyde level in the environment.

DETAILED DESCRIPTION OF THE INVENTION

Figure 1A:
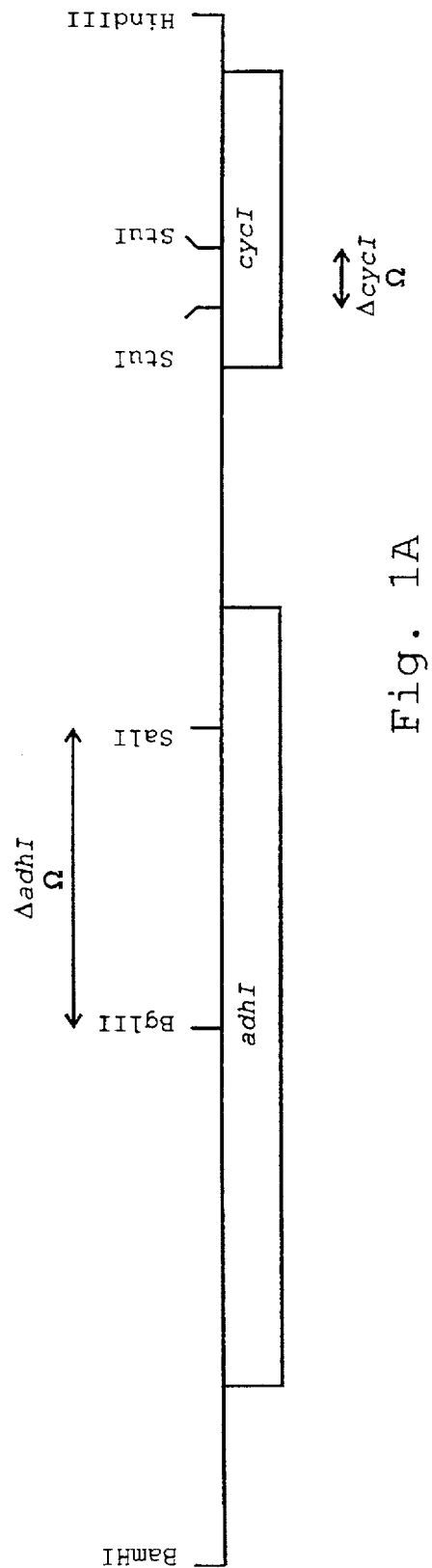
FIG. 1a shows a partial restriction map of a portion of the R. sphaeroides genome that encodes the adhI-cycI operon.

In its broadest sense, the present invention is a gene regulation system active in a bacterial host cell that can be induced at the transcriptional level when the cell is exposed to formaldehyde. The transcriptional regulation scheme contemplated herein is a two-component regulatory system of the type reviewed by Bourret, R. B. et al., Annual Rev.; Biochem; 60:401–411 (1991), incorporated herein by reference, and by Parkinson, J. S. and E. C. Kofoid, Annual Rev. Genetics, 26:71–112 (1992), incorporated herein by reference.

In brief, a two-component regulatory system includes a sensor protein that specifically detects a target molecule and, upon detection, transmits a signal to a trans-acting effector or regulatory molecule that modulates activity elsewhere in a cell. Modulation can be at the transcriptional, translational, or functional level. In such systems, the signal is generally transmitted by means of autophosphorylation of the sensor followed by transphosphorylation by the sensor of the regulatory molecule. In the present system, the regulatory molecule is a DNA-binding repressor protein. Reference herein to the repressor protein, the effector protein or regulatory protein are all intended to refer to this molecule.

In some two-component regulation systems, the sensor molecule is not a single protein but is, in fact, a complex of two proteins, both of which are important to the sensing function. When this is the case, the additional protein is typically encoded in the same operon as the major sensor protein. Although there is no evidence that an additional protein is used by the present regulatory system, if such an additional protein is a part of the formaldehyde-inducible system, it would likely be encoded on the same piece of cloned genetic material as the repressor and sensor reported herein, since a clone described herein has been demonstrated to contribute all necessary functions of the regulatory system. The competent DNA fragment is part of genomic clone pUI8017 obtained from a genomic cosmid library of wild-type Rhodobacter sphaeroides (strain 2.4.1) DNA. The genomic library was described by Dryden, S. and S. Kaplan, "Localization and Structural analysis of the ribosomal RNA operons of Rhodobacter sphaeroides," N. A. R. 18:7267 (1990), incorporated herein by reference. The genomic clone pUI8017 was prepared in cosmid vector pLA2917, which was itself described by Allen, L. N. and R. S. Hanson, "Construction of Broad-Host-Range Cosmid Cloning Vectors: Identification of Genes Necessary for Growth of Methylobacterium organophilum on Methanol," J. Bact. 161:955 (1985), incorporated herein by reference.

It is understood that the invention in its broadest forms is not intended to be limited to the transcription and translation of any particular indicator gene operably linked to the formaldehyde-inducible promoter that is regulated in the regulatory system.

Moreover, strictly speaking, formaldehyde itself may not be the target molecule that induces the regulatory system. Rather, it is likely that a adduct of formaldehyde, such as S-hydroxy methyl glutathione (HMGSH), may actually be the target molecule of the system described herein. However, it is abundantly clear that the system is responsive to the presence of formaldehyde and for purposes of this application, convenient reference is made to induction "by formaldehyde," with the understanding that subsequent studies may reveal that the true target molecule is not formaldehyde but rather a related molecule or adduct.

The formaldehyde that induces the expression system can derive from any source, including industrial or commercial waste, or a biological or chemical degradation product of such waste. For example, the system can respond to a methyl donor (such as choline, sarcosine, methionine, O-methylated amino acids, methanol, methyl halides, or several N-, O-, or S-methylated xenobiotics) if the bacterial host cell has the facility to convert the methyl donor into formaldehyde or if another conversion mechanism is provided.

In the present system, when the repressor is bound to the promoter region there is virtually no transcription of the operably attached gene in the absence of formaldehyde. For purposes of this invention, "virtually no transcription" means less than 10% and preferably less than 1% of the transcription observed in the induced, or de-repressed, state. For purposes of this patent application, "induction" means an increase in transcription from the formaldehyde-inducible promoter of more than 10-fold from its uninduced state and preferably an increase of greater than 100-fold. Transcriptional increases as high as about 1000-fold are contemplated.

The system is responsive to formaldehyde even at very low levels. Micromolar or higher quantities of formaldehyde are sufficient in aqueous environments to induce the expression system of the present invention. Comparable levels are likely sufficient in other environments as well. At a lower limit, the system can be induced in the presence of less than 100 micromolar and more preferably less than 10 micromolar formaldehyde in R. sphaeroides. The lower induction limit is thought to be less than 1 micromolar (1 ppm), say 0.01 micromolar. In other organisms, the induction level may vary, depending upon the threshold level of toxicity of formaldehyde to the organism. It is, of course, understood that the upper and lower induction limits and the window of effectiveness are readily determined in any organism using standard analytical methods.

The invention finds particular utility as a biosensor system by which the presence of formaldehyde in an environment is revealed by the regulated production of a detectable protein. If the invention is used for formaldehyde detection, a suitable bacterial strain is added to an environmental sample to be analyzed, and the sample is monitored for changes in an indicator gene, as is described in more detail below.

Alternatively, formaldehyde can be converted into other substances to promote a remediating effect upon the environment when the indicator gene is replaced by a gene that can oxidize formaldehyde. In such a method, it would be possible to observe a decrease in formaldehyde level in the environment.

For purposes of this application, a "sample" can be an aliquot suitable for laboratory analysis, but can equally well be a larger-scale location for which remediation is desired, such as a body of water which can include, but is not limited to, a water treatment facility, a lake, a pond, a river or a stream.

In a related method, the ability to respond to the presence of formaldehyde can also be used to effect production of a desired protein for reasons other than formaldehyde detection or remediation. For example, it may be desirable to induce one or more cellular pathways to degrade other agents commonly found in formaldehyde-containing environments. In such a method, it is also envisioned that a cascade of such responses could be carried out in a single bacterial cell type.

The methods may be practiced by providing the bacterial cells on an immobilized surface or substrate or the cells can be unattached.

In addition to the above-noted methods, the present invention also provides a genetic construct for use in the methods. By providing a genetic construct, transfer of the disclosed system into other organisms is facilitated. The exemplified embodiment of the system described herein is operative in wild type *Rhodobacter sphaeroides*, a purple, non-sulfur photosynthetic bacterium typically found in low oxygen aquatic environments and in mutants thereof that retain the relevant genes as described herein. Moreover, using genetic materials of the type disclosed herein, it is readily possible to transfer the genetic components of this system into bacterial host cells including facultative or strict anaerobes and aerobes that populate, for example, soil, air, high acid (*acidophiles*), or high salt (*halophiles*) environments and the like, and into bacterial strains that selectively populate hot and cold temperature environments. Bergey's Manual of Determinative Bacteriology, 9th ed., Williams & Wilkins, Baltimore, Md., John G. Holt, ed. (1994), incorporated herein by reference, is an authoritative index of known bacteria that includes lists of various organisms meeting these criteria. Thus, in addition to using *Rhodobacter sphaeroides* in a remediation or detection assay, other bacterial cells containing non-native constructs of the type described herein are also within the scope of the present invention.

A suitable genetic construct includes an indicator or effector gene under the control of the formaldehyde-inducible promoter, which can be a gene suitable for detection or remediation of formaldehyde or any other gene whose product can be detected. If a self-replicating construct is used, the construct also includes those additional elements, such as an origin of replication and a selectable marker, which are necessary for replication and maintenance in a bacterial host. Alternative constructs could be incorporated directly into the chromosomal material of the host organism. Other genes may also be provided on the construct without interfering with the present invention. The construct can be, for example, a plasmid, cosmid or phagemid.

It is understood that the formaldehyde-inducibility depends upon both the promoter and the operably linked cis-acting operator element near the promoter (preferably provided within 50 nucleotides, more preferably within 25 nucleotides, of the promoter sequence). The operator is thought to be the binding site of the regulatory protein described elsewhere herein and is also believed to be the inverted repeat sequence identified elsewhere herein. The operator, which is encoded on the same exemplified genetic fragment as the promoter, is physically separable from the promoter and has separate utility as a genetic element that may be placed near any other promoter to confer formaldehyde-inducibility upon that other promoter. This may be desirable in a particular expression system where formaldehyde inducibility is desired but where a stronger (or weaker) promoter than the one that naturally promotes transcription of the R. *sphaeroides* adhI-cycI operon is also desired. It may also be useful for transfer to other organisms where other promoters are preferred.

For purposes of convenience in this application, all references to the formaldehyde-inducible promoter, or to the "promoter/operator" are intended to include reference to the cis-acting operator sequence, with the understanding that the two elements, while physically linked, are separable and contribute separate functionality to the system described herein. Reference herein to the promoter and operator working together to direct transcription are intended to mean that transcription from the promoter occurs only when the regulatory protein is not bound to the nearby operator sequence, and moreover that when the regulatory protein is bound to the operator, virtually no transcription from the promoter can take place.

A suitable formaldehyde-inducible promoter region that can be isolated from the upstream portion of an operon from the *Rhodobacter sphaeroides* genome that encodes adhI-cycI, is shown as bases numbered 1–345 of SEQ. ID. NO:1. The portion of the *R. sphaeroides* genome that contains the adhI-cycI operon is shown schematically in the partial restriction map of FIG. 1a. The promoter portion of the operon is highlighted in FIG. 2. In vivo, two transcription products covering the adhI-cycI operon are observed, and, indeed, two genetic segments recognized as having promoter activity are present in that portion of SEQ ID NO:1. Relative to the adhI translational start site (base number 346 of SEQ ID NO:1), the two in vivo transcripts map to positions −267 and −49, which correspond in SEQ ID NO:1 to base numbers 79 and 297, respectively.

Although both promoters may be present in a genetic construct within the scope of the present invention, only the promoter responsible for the −49 transcript is sensitive to the regulatory network described herein and to the controlling metabolic signals.

The formaldehyde-inducible promoter/operator is under the proximate control of a DNA-binding protein that binds to, and negatively regulates, the promoter described above, when formaldehyde is absent from the environment. Although the specific nucleotides of the operator that reversibly interact with the repressor protein have not been determined with specificity, an inverted repeat sequence between the −10 sequence and the translation start sequence is thought to be the binding site of the repressor molecule. The inverted repeat portion is shown between bases 289 and 310.

It is not scientifically possible to rule out the possibility that an additional set of induction proteins may also be involved in induction of this expression system. Therefore, total induction in the system may be higher if additional activating proteins are available. In any event, significant induction is observed in the system as described. Work is in progress to evaluate the likelihood of this possibility.

In view of the preceding analysis of the promoter region, the following portions of SEQ ID NO:1 are suitable promoter sequences, listed in order of increasing preference: bases 1 to 345, bases 85 to 345, bases 109 to 345, bases 128 to 345, bases 157 to 345, bases 173 to 345, bases 196 to 345, bases 220 to 345, and bases 241 to 345. An even smaller portion that comprises the −10 and −35 regions and the inverted repeat may also function adequately. It is probable that the promoter function resides entirely in the region between bases 1 and 310, and thus, yet more preferred promoter regions are those identified above in this paragraph, except having a 3' end at base 310 rather than at base 345.

It will be appreciated by one of ordinary skill in the art upon consideration of this specification that only certain nucleotides of the promoter region are involved in the interaction with the formaldehyde-inducible regulatory system described herein and that, as long as the general requirements of all bacterial transcriptional promoters such as −35 and −10 sequences (ATGCCG and ATAGGT, respectively, in the exemplified embodiment) are provided, other portions of the promoter region may be altered, modified or deleted without departing from the spirit of the present invention, as long as the ability to modulate transcription in response to formaldehyde is maintained. Promoter activity can also be modified, for example, by altering the −35 and −10 sequences so that they have greater similarity to known consensus sequences.

Figure 1B:
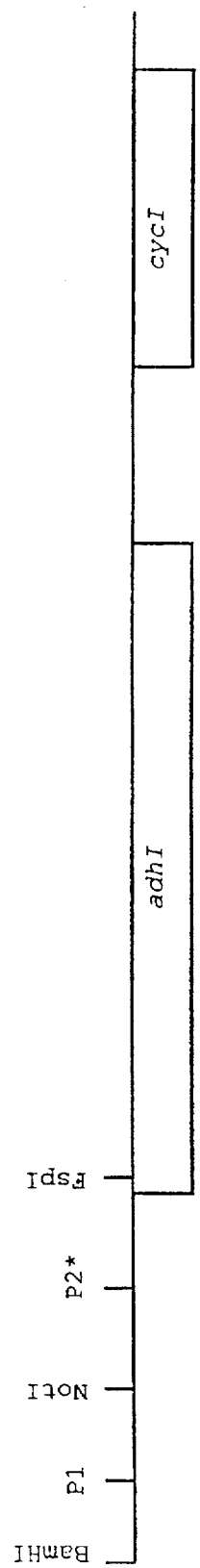
FIG. 1b shows a partial restriction map of the promoter portion of the adhI-cycI operon.

The promoter can actively promote transcription without additional contribution of transcription-enhancing activator sequences, although these may be provided in a suitable construct. Other sequences that contribute to transcription are sometimes found in the 5' untranslated region upstream from a coding region. Thus, the inventors cannot rule out the possibility that other sequences upstream from the coding sequence shown in FIG. 1 may contribute to regulation of this promoter.

Likewise, it is also to be appreciated that genetic manipulation techniques may be applied to the promoter region to alter, particularly to strengthen, repressor binding. The binding of the repressor to the site can be altered by substituting bases in the binding site, thought to be the inverted repeat. It is also specifically envisioned that coordinate changes to both the promoter and its repressor can be made without departing from the spirit of the invention. By so modifying the promoter, an environment is created wherein a very tightly bound repressor protein further reduces the level of baseline transcription while the modified −35 and −10 sequences bring about higher transcription levels when the repressor is removed. The net effect will be an improved signal-to-noise ratio which will facilitate the detection of even smaller amounts of the target molecule.

It is unknown whether there is a preferred spatial or distance relationship between the inducible promoter and gene positioned downstream from the promoter, although the natural spatial relationship is considered to be preferred.

A vast number of genes can be linked to the inducible promoter. The selection of a gene for linkage is entirely dependent upon the desired response to the presence of formaldehyde, which may relate to detection or remediation of formaldehyde or may effect an entirely different activity. Generally speaking, a suitable gene is a gene that encodes a detectable protein, referred to herein as an "indicator gene." For purposes of this patent application, the term "indicator" or "indicator gene" is intended to include all bacterial detection systems, without regard to whether the molecule detected is a product of the indicator gene itself or is a substrate for the gene product. The art is replete with known indicator genes and systems for detecting their transcription and any of such genes can be effectively used to monitor activity of the inducible promoter of the present invention. For example, three commonly used detection systems rely upon the lacZ gene, luciferase gene, and the Green Fluorescent Protein gene.

The detected molecule can be formaldehyde if the attached indicator gene is gene is a Class III alcohol dehydrogenase enzyme, also called a "glutathione-dependent formaldehyde-dehydrogenase" or "GSH-FDH" enzyme capable of dehydrogenating formaldehyde to other byproducts. Such genes are preferred indicator genes for use in a formaldehyde remediation method. Many such GSH-FDH genes are known and have been isolated from bacterial and eukaryotic sources. GSH-FDH genes having activity against formaldehyde are described, for example by Jornvall, H. et al., *Eur. J. Biochem.* 167:195 (1987), by Koivusalo, M. and L. Uotila, in *Enz. and Mol. Biol. of Carbonyl Metabolism 3 and 4*, Plenum Press, NY, eds. H. Weiner et al. (1990), by Engeland, K. et al., *Proc. Natl. Acad. Sci. USA* 90:2491 (1993), by Green, et al., *J.B.C.* 268:7792 (1993), and by Estonius, M. et al., *Biochemistry* 33:15080 (1994), all of which are incorporated herein by reference. Certain of these publications also describe the modification of other genes by point mutation to bring about formaldehyde-specific activity. Thus, not only are the classic GSH-FDH enzymes suitable for linkage to the promoter, but it will also be understood that other alcohol dehydrogenases, suitably modified can also be used in a formaldehyde remediation system. The source of the gene is not limiting, as long as the protein encoded by the gene is made and folded to form a protein that functions as desired in a bacterial host cell. Any such GSH-FDH gene that can be expressed in a bacterial host and which confers formaldehyde-specific dehydrogenating activity is acceptable. GSH-FDH enzymes also have activity against long chain hydroxylated fatty acids having between 8 and 16 carbons (e.g., 12-hydroxydodecanoic acid) and long chain alcohols having an alcohol group (OH) at the terminal carbon. The system disclosed herein could be adapted to reduce levels of such materials as well.

A suitable GSH-FDH gene is the adhI formaldehyde dehydrogenase gene of *Rhodobacter sphaeroides* which is co-regulated in vivo with a downstream gene encoding isocytochrome $c_2$ (cycI). The sequence of the adhI gene is shown herein as bases 346–1476 of SEQ. ID. NO:1. An arginine residue corresponding to the arginine at position 110 of AdhI has been shown to be important for enzymatic activity of other GSH-FDH enzymes against some substrates (including formaldehyde) and may be important to the activity of this gene product as well. Furthermore, AdhI has nine out of ten residues predicted to be conserved in the substrate binding cleft of GSH-FDH enzymes.

The adhI gene can be varied by addition, deletion or mutation of sequences that do not affect formaldehyde dehydrogenation. As evidence of the variation that is acceptable in such genes, *Rhodobacter sphaeroides* adhI contains an 18 nucleotide long insertion (bases 1111–1128) relative to known eukaryotic GSH-FDH genes that does not alter the ability of the encoded enzyme to oxidize formaldehyde.

A preferred repressor protein has the amino acid sequence shown in SEQ ID NO:4, which shows significant homology to response regulators of two-component regulatory systems. The protein sequence likely also includes one or two methionine codons immediately upstream from the indicated sequence. The sequence possesses all of the most highly conserved residues and many of the lesser-conserved residues of the N-terminal consensus sequence proposed by Volz, Biochemistry 32: 11741 (1993). The deduced amino acid sequence also possesses a C-terminal LuxR family helix-turn-helix DNA binding motif, shown between amino acids 173 and 200 of SEQ ID NO:4. The DNA binding motif and the structural relationship to other response regulating portions of two-component regulatory systems, suggests that this protein binds at or near the formaldehyde-specific promoter, and negatively regulates transcription from the promoter, as was noted above.

The DNA-binding repressor protein can be provided by a genetic construct containing an expressible DNA sequence that encodes a polypeptide capable of regulating transcription from the formaldehyde specific promoter. A suitable and preferred DNA fragment that encodes such a repressor molecule is shown in SEQ ID NO 3. It is noted that two ATG methionine-encoding codons immediately precede the coding sequence and that one or both likely contribute to the coding portion of the sequence.

Of course it is understood from consideration of this specification, that the entire repressor protein molecule or gene may not be required for formaldehyde-specific regulation. As will become apparent, the only required amino acids of the regulator protein (or the corresponding nucleic acid sequences in a genetic construct encoding such a protein) are the portions of the protein used for DNA binding at or near the promoter region and the portions used for receiving a phosphorylation signal from a formaldehyde-specific sensor molecule. All modifications, alterations, or deletions of the repressor molecule that do not otherwise interfere with the ability of the molecule to function as described are intended to fall within the scope of the present invention. It is believed that the binding portion of the repressor protein molecule is the helix-turn-helix portion between amino acids 173 and 200 of SEQ ID NO:4. It is further believed that the site of phosphorylation is the aspartate residue at amino acid 62 of the protein shown in SEQ ID NO:4, encoded by the triplet that begins at base 398 of SEQ ID NO:3.

The next aspect of the invention is the ability to sense the presence of environmental formaldehyde in a sample and to direct a signal to the repressor protein in response thereto. In one embodiment of the system disclosed herein, formaldehyde recognition is provided by a formaldehyde-dependent kinase sensor molecule that transphosphorylates the regulator component of the two-component regulatory system after exposure to formaldehyde. A suitable preliminary gene sequence, which encodes such a protein is shown in SEQ ID NO:5. Although it is believed that the entire sequence of SEQ ID NO:5 is a coding sequence, the entire sequence has not been so designated because the sequence presented is preliminary. However, it has been determined that an internal portion of the presented sequence (between bases 2113 to 2400) corresponds well to a conserved portion of other known sensor proteins. The translated portion is shown in SEQ ID NO:6. Based upon this comparative analysis, it is expected that the portion of the molecule having specificity for formaldehyde will be encoded by the first 2000, and more likely by the first 1500, bases of SEQ ID NO:5.

The available sequence data and restriction map are sufficient to permit one of ordinary skill, using routine techniques of molecular biology, to obtain the gene encoding the sensor protein by preparing and using probes complementary to the presented sequence of SEQ ID NO:5, particularly to the first 2000 or first 1500 bases. The nature of probing is such that the few mismatches that might arise from an inaccuracy in the presented sequence would not prevent one from obtaining the desired gene.

Figure 2:
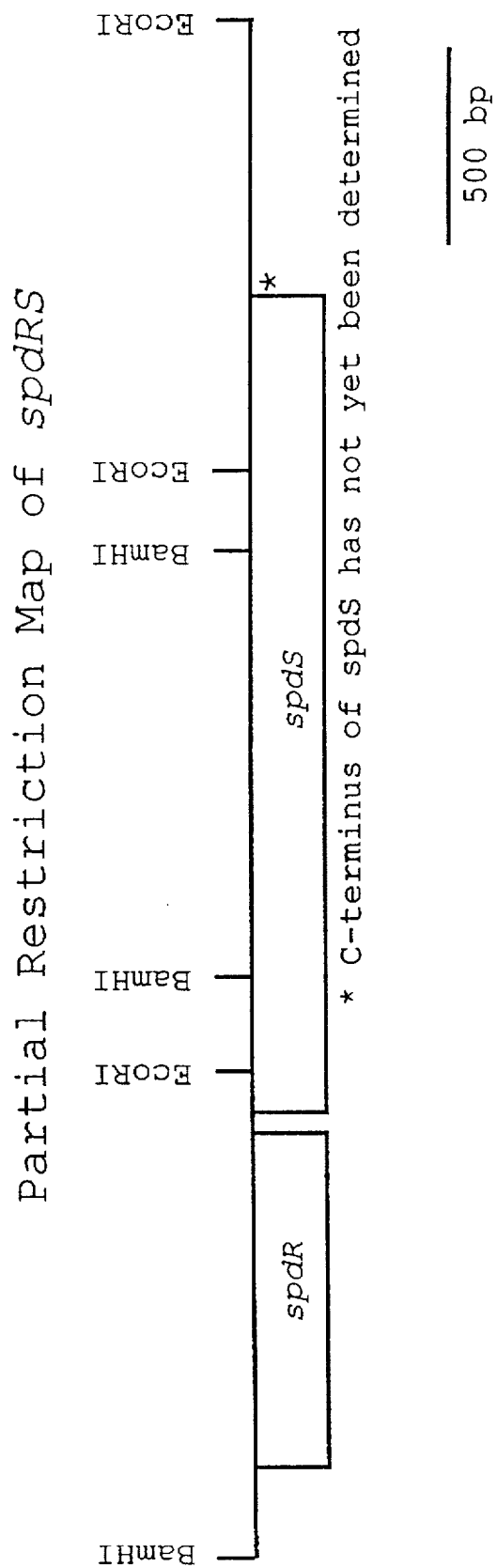
FIG. 2 shows a partial restriction map of genomic clone pUI8017 that contains the gene that encodes the repressor protein (tentatively named SpdR) and the gene that encodes the sensor protein (tentatively named SpdS).

In nature, the gene encoding the sensor protein and the gene encoding the repressor protein are linked members of a single operon. FIG. 2 shows a partial restriction map of genomic clone pUI8017 that contains the gene that encodes the repressor protein (tentatively named SpdR) and the gene that encodes the sensor protein (tentatively named SpdS). This portion of a bacterial genome can be obtained by using a genetic probe corresponding to the exemplified sequence or any portion thereof. Since organisms may contain genes related to the spdr and spds genes, suitable probing stringency conditions should be determined that detect only the desired gene regions.

Near the carboxy terminal end of the sensor protein sequence, at amino acid 19 of SEQ ID NO:6, is a histidine residue that is autophosphorylated. The phosphate is then transferred to an aspartate residue of the DNA-bound repressor molecule described elsewhere herein. Because the phosphorylated repressor molecule has reduced ability to bind to the promoter/operator region, its attachment to the DNA is reduced, facilitating transcription of the operably-linked gene.

It is understood by those of ordinary skill that certain variation in the size or sequence of the sensor protein (and in the corresponding genetic material encoding the sensor protein) will not interfere with the functions thereof. Such changes, modifications, additions and deletions are contemplated to fall within the scope of the present invention, as long as the protein retains a competent formaldehyde-sensing portion and an effector portion.

The competence of the inducible system can be judged by any measure of increased transcription of the operably linked indicator gene. Increased transcription can be measured directly by measuring RNA level, or indirectly by observing an increase in the level of the protein encoded by the indicator gene. Alternatively, a change in an indicator molecule affected by the attached gene can be measured. Such a change can be in color, concentration, fluorescence, optical density or other attribute.

The preferred promoter DNA, repressor coding sequence (and corresponding protein sequence), and sensor coding sequence (and corresponding protein sequence) were isolated and purified from the genome of wild type *Rhodobacter sphaeroides*. It is believed that, using this specification as a guide, the promoter, the sensor, and/or the repressor within the scope of the present invention can now readily be purified from other organisms capable of growth on formaldehyde or on a carbon source that can be degraded to formaldehyde, such as methanol. Thus, the invention is not limited to these molecules prepared or obtained from a particular source. Rather, one of ordinary skill, using routine techniques for locating DNA that is structurally related at a sequence level, can prepare a sequence specific probing strategy, such as a PCR probe analysis, to retrieve these sequences from other *Rhodobacter sphaeroides* strains, other Rhodospirillaceae, other bacterial organisms, and a wide variety of eukaryotic organisms known to have mechanisms for formaldehyde oxidation.

Formaldehyde oxidation is ubiquitous and GSH-FDH enzymes are found in many organisms. Such organisms are considered likely to contain such GSH-FDH genes and may contain the regulatory genes as well. Also, formaldehyde dehydrogenase activity has been observed in formaldehyde-resistant Enterobacteriaceae. Kaulfer, P. and A. Marquardt, FEMS Microbiol. Letters 79:335–338 (1991). Bacterial, plant, yeast, and animal (including human) GSH-FDH enzymes have been shown to catalyze the NAD-dependent oxidation of HMGSH and long chain hydroxylated fatty acids and alcohols. The nucleic acid sequence of a GSH-FDH gene from *Paracoccus denitrificans* has recently been reported by Ras, et al., J. Bact. 177:247–251 (1995), that shares 89% amino acid identity and 95% amino acid similarity to AdhI of *Rhodobacter sphaeroides*, and is predicted to be a useful effector gene for linkage to the inducible promoter of this system.

While identical sequences isolated from a different organism would certainly come within the scope of the present invention, it is also understood that complete structural relatedness is not necessary. As has been described above for each element, only that level of structural relatedness sufficient to maintain the functionality of the invention is required. It is contemplated and understood that certain nucleic acid substitutions in the operator, promoter, indicator gene, sensor gene and repressor gene have no effect or only moderate effect upon protein production and function. Indeed, given the well understood redundancy in the genetic code, certain nucleic acid substitutions are completely silent with respect to encoded protein sequences. All such substitutions to any of the various genetic constructs and proteins described herein are within the scope of the present invention.

It is not necessary that the components of the formaldehyde-inducible expression system be obtained from a single source, but rather, individual elements can be obtained from disparate sources or can be synthesized in vitro. It is also understood that, although the sequences presented herein are the preferred sequences known to the inventors for carrying out the invention, it is specifically envisioned that strains carrying mutations in any element of the system may be sought, using techniques available to those skilled in the art, to optimize the effect of the described expression system upon the promoter.

It is also envisioned that on the basis of this disclosure, the genetic components of this expression system can be created or combined in any combination in vitro using well understood tools available to a molecular biologist. It is routine to construct an expressible gene construct incorporating a promoter operably linked upstream (5') to a coding region encoding an indicator protein of interest. A suitable promoter sequence is provided which can direct the inducible transcription of any attached gene. To achieve the desired inducible regulatory effect in the disclosed system, it is desirable, in the uninduced state, that there be virtually no transcription of the gene of interest. Accordingly, it is desired that an amount of the repressor molecule be available to effectively keep the promoter inactive in bacterial host cells in which the system is operative. Thus, expression of the gene encoding the repressor molecule can be under the transcriptional control of a constitutive promoter. Since the sensor protein is required to sense formaldehyde in the environment and since the regulatory system does not induce appreciable transcription until formaldehyde is detected, the gene encoding the sensor protein can also be expressed constitutively in the bacterial host cells and can be under the transcriptional control of any promoter that can direct the transcription of the repressor protein. A suitable promoter can be determined for each strain into which the system will be introduced. For example, the *E. coli* $P_{lac}$ promoter is functional in many, but not all, bacterial cell hosts.

It is further envisioned that if the expression system of the present invention is incorporated into a larger regulatory scheme, it is certainly possible to regulate the expression of the sensor or regulatory proteins as desired by selecting other promoters to govern transcription in a non-constitutive manner.

The present invention will be more completely understood upon consideration of the following Examples which are intended to be exemplary and in no way limiting on the invention.

EXAMPLES

Bacterial Strains, Plasmids and Growth Conditions

Bacterial strains and plasmids used in this work are listed in Table 1. *E. coli* strains were grown at 37° C. in Luria-Bertani medium. *R. sphaeroides* strains were grown in Sistrom's minimal medium A (37) at 32° C. Supplements were sterilized separately and added at the following concentrations: ampicillin, 100 µg/ml; tetracycline, 1 µg/ml for *R. sphaeroides* and 10 µg/ml for *E. coli*; spectinomycin, 25 µg/ml/ and isopropyl-β-D-thiogalactopyranoside (IPTG), 1 mM.

DNA Sequence Analysis

DNA sequencing with Taq DNA polymerase (Promega, Inc., Madison, Wis.) was performed as suggested by the manufacturer with deaza nucleoside triphosphate reagent kits. Most of the DNA sequence was obtained with lac specific primers and double-stranded derivatives of pUC18 or pUC19 vectors. Primers specific to *R. sphaeroides* DNA were used to aid in analyzing regions with strong secondary structure or to complete the generation of double-stranded DNA sequence. DNA and the subsequent protein sequence were analyzed with software from Genetics Computer Group, Madison, Wis. The DNA sequence fragment from the BamHI to SalI restriction endonuclease sites shown in FIG. 1 (SEQ ID NO:1) will be available in the Genome Sequence Data Base under accession number L47326.

GSH-FDH Activity Assays

GSH-FDH activity can be detected in crude cell extracts using the following detection scheme. Cultures of either *R. sphaeroides* or IPTG-induced *E. coli* cells can be grown aerobically to late log-early stationary phase, harvested (8,000×g), and washed with 150 mM sodium phosphate buffer (pH 8.5). Cell pellets can be stored at −20° C. until the assay is performed. Prior to lysis, the thawed cell pellet is suspended in 5 ml of 150 mM sodium phosphate buffer (pH 8.5) containing 0.1% phenylmethylsulfonylfluoride as a protease inhibitor. The cells are lysed by two passes through a French press at 18,000 psi. DNase is added to a final concentration of 5 μg/ml, and the lysate is incubated on ice for 30 minutes. Cell debris is removed by centrifugation at 10,000×g for 15 minutes and the supernatant is assayed for GSH-FDH activity. Protein concentrations can be determined by the SDS modification of the Folin phenol method using bovine serum albumin as a standard.

Assays for GSH-FDH activity using S-hydroxy methylglutathione (HMGSH) as a substrate can be performed as described by Uotila and Koviusalo, Methods Enzymol. 77:314–320 (1981), with the following modifications: the final concentration of sodium phosphate buffer (pH 8.5) is 150 mM, the final concentration of NAD is 1 mM, and 0.01 to 1 mg of crude cell extract protein is added. A typical assay using other potential GSH-FDH substrates includes a volume of cell extract (containing 0.1 to 1 mg total protein), 150 mM sodium phosphate buffer (pH 8.5), 1 mM NAD as an electron acceptor, and appropriate concentration of substrate [1 mM for long chain (>5 aliphatic carbons) alcohols and acids, 0.2M to 1M for short chain (<5 aliphatic carbons) alcohols]. In all cases, enzyme activity can be measured spectrophotometrically by the time-dependent reduction of NAD and corresponding increase in absorbance at 340 nm at room temperature using a SLM DW2000 spectrophotometer. A unit of GSH-FDH activity is defined as the amount of enzyme required to reduce 1 μmole of NAD per minute.

The size of an active GSH-FDH protein can be determined by activity gel electrophoresis. Following native polyacrylamide gel electrophoresis, zymograms for GSH-FDH activity can be obtained by adding a half volume of a loading solution, containing 40% (w/v) sucrose plus a trace of bromophenol blue to an appropriate volume of cell extract prior to loading the gel. Proteins can be separated on a 5% stacking gel and 10% separating gel using Tris-HCl buffer (pH 8.3) in the gel and Tris-glycine buffer (pH 8.8) in the electrode vessels with an applied current of 10–20 mA/gel at 4° C. for a minimum of 14 hours.

Following electrophoresis, the gel is stained for GSH-FDH activity using a solution of 70 mM sodium phosphate buffer (pH 7.5); 500 mM KCl; 1.2 mM NAD; 4.8 mM formaldehyde; 1 mM glutathione; 0.4 mg/ml nitroblue tetrazolium and 0.03 mg/ml phenylmethylsulfate with gentle shaking at 37° C. Enzyme activity can be visualized in less than an hour and the gel can be rinsed in distilled water prior to photographing.

Promoter Isolation

The location of the promoters upstream from the *R. sphaeroides* adhI gene were determined by primer extension analysis. RNA from aerobic *R. sphaeroides* cultures was prepared as previously described by Zhu and Kaplan, J. Bacteriol. 162:925–932 (1985). An oligonucleotide (4'-ATTGACCTCCATGATCTCGA-3') (SEQ ID NO:7) complementary to a region 42 nucleotides downstream of the adhI translational start codon was used for primer extension assays (Genosys, The Woodlands, Tex.). Primer (25 pmole) and RNA (15 μg) were hybridized at 45° C. for 15 minutes; then a solution of nucleotide triphosphates, reverse transcriptase, and actinomycin D was added and incubated for 30 minutes at 45° C. The reaction was stopped by adding a formamide-EDTA loading buffer. Samples were boiled prior to loading on a 6% denaturing polyacrylamide gel. Putative transcription initiation sites were mapped by comparison to DNA sequencing reactions generated with the same primer on an adhI template.

Preference for Induction by Formaldehyde

Figure 3:
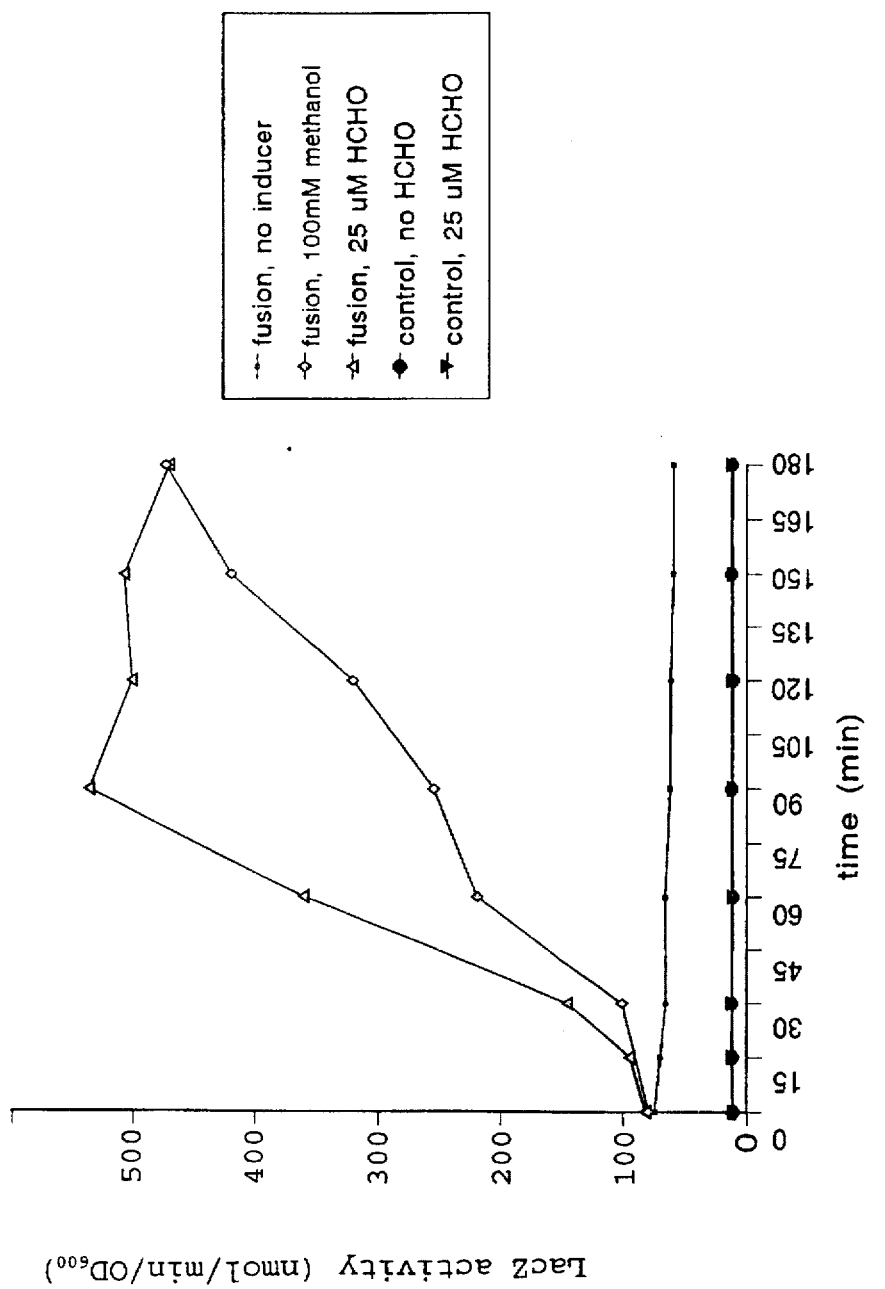
FIG. 3 depicts the induction by methanol and formaldehyde of an indicator gene (lacZ) operably linked to the promoter and operator described herein.

FIG. 3 depicts the activity of the full-length adhI promoter when the promoter is fused to an indicator gene (lacZ). Wild type cells carrying the full length adhI promoter region fused to lacZ were grown to mid-log phase. Then, either methanol or formaldehyde was added to the media and beta-galactosidase was measured during a three hour time course. Without any inducer, activity of LacZ encoded by the test construct was low and invariant over time. In contrast, in the presence of 25 μM formaldehyde, the lacZ gene was induced to produce as much as about 425 lacZ activity units (nMol/min/OD600) by about 90 minutes. This rate was maintained for at least another 1.5 hours. Using 100 mM methanol as the inducer, it took almost 3 hours to reach this level of LacZ activity.

To demonstrate the specificity of the response, the control included a cycA gene operably fused to the *E. coli* lacZ gene.

---

We claim:

1. A genetic construct comprising:

a protein-encoding indicator gene; and a transcriptional adhI promoter from *Rhodobacter sphaeroides* operably linked to the indicator gene; and a cis-acting operator from *R. sphaeroides* operably linked to the promoter, the promoter and operator together specifically directing transcription of the indicator gene in a *Rhodobacter sphaeroides* cell comprising a protein that senses formaldehyde and a trans-acting protein that modulates transcription from the promoter in response to a signal from the protein that senses formaldehyde.

2. The genetic construct as claimed in claim 1 wherein the transcriptional promoter and operator are located within the sequence between nucleotides 1 and 310 of SEQ ID NO:1.

3. The genetic construct as claimed in claim 1 wherein the transcriptional promoter and operator are located within the sequence between nucleotides 220 and 310 of SEQ ID NO:1.

4. The genetic construct as claimed in claim 1 wherein the transcriptional promoter and operator are located within the sequence between nucleotides 241 and 310 of SEQ ID NO:1.

5. The genetic construct as claimed in claim 1 wherein the indicator gene encodes a detectable protein.

6. The genetic construct as claimed in claim 1 wherein the indicator gene encodes a protein that acts upon a detectable substrate.

7. The genetic construct as claimed in claim 1 wherein the indicator gene is a GSH-FDH gene.

8. The genetic construct as claimed in claim 7 wherein the indicator gene is *Rhodobacter sphaeroides* adhI.

9. A *Rhodobacter sphaeroides* cell comprising:

a non-native genetic construct comprising a protein-encoding indicator gene, a transcriptional adhI promoter from *R. sphaeroides* operably linked to the indicator gene, and a cis-acting adhI operator from *R. sphaeroides* operably linked to the promoter;

a protein that senses formaldehyde; and a trans-acting regulatory protein that modulates transcription of the indicator gene from the transcriptional promoter in response to a signal from the protein that senses formaldehyde, wherein the promoter and operator together specifically direct transcription of the indicator gene when the cell is exposed to formaldehyde.

10. The cell as claimed in claim 9 wherein the transcriptional promoter and operator are located within the sequence between nucleotides 1 and 310 of SEQ ID NO:1.

11. The cell as claimed in claim 9 wherein the transcriptional promoter and operator are located within the sequence between nucleotides 220 and 310 of SEQ ID NO:1.

12. The cell as claimed in claim 9 wherein the transcriptional promoter and operator are located within the sequence between nucleotides 241 and 310 of SEQ ID NO:1.

13. The cell as claimed in claim 9 wherein the indicator gene encodes a detectable protein.

14. The cell as claimed in claim 9 wherein the indicator gene encodes a protein that acts upon a detectable substrate.

15. The cell as claimed in claim 9 wherein the indicator gene is a GSH-FDH gene.

16. The cell as claimed in claim 9 further comprising a genetic construct encoding the sensing protein.

17. The cell as claimed in claim 9 further comprising a genetic construct encoding the trans-acting regulatory protein.

18. The cell as claimed in claim 15 wherein the indicator gene is *Rhodobacter sphaeroides* adhI.

19. The cell as claimed in claim 16 wherein the genetic construct encoding the sensing protein comprises a sequence of SEQ ID NO:5 from bases 1 to 2000.

20. The cell as claimed in claim 17 wherein the genetic construct encoding the trans-acting regulatory protein comprises a sequence of SEQ ID NO:3 from bases 220 to 892.

21. A genetic construct encoding a *Rhodobacter sphaeroides* trans-acting regulatory protein that modulates transcription of an indicator gene from a transcriptional promoter in response to a signal from a *R. sphaeroides* protein that senses formaldehyde, the DNA comprising a sequence of SEQ ID NO:3 from bases 220 to 892.

22. A genetic construct encoding a *Rhodobacter sphaeroides* protein that senses formaldehyde, the DNA comprising a sequence of SEQ ID NO:5 from bases 1 to 2000.

23. A genetic construct comprising:

a transcriptional promoter active in a *Rhodobacter sphaeroides* host cell; and a gene encoding a protein that senses formaldehyde in a sample and directs a signal to a repressor protein in response thereto, the gene comprising a sequence of SEQ ID NO:5 from bases 1 to 2000.

24. A genetic construct comprising:

a transcriptional promoter active in a *Rhodobacter sphaeroides* host cell; and a gene encoding a trans-acting transcriptional repressor protein that de-represses transcription in response to a signal from a protein that senses the presence of formaldehyde, the gene comprising a sequence of SEQ ID NO:3 from bases 220 to 892.

* * * * *